(12) United States Patent
    Bales

(10) Patent No.: US 12,661,149 B2
(45) Date of Patent: Jun. 23, 2026

(54) SPINAL IMPLANT SYSTEM AND METHOD

(71) Applicant: Warsaw Orthopedic, Inc., Warsaw, IN (US)

(72) Inventor: Joel Bales, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 511 days.

(21) Appl. No.: 18/123,457

(22) Filed: Mar. 20, 2023

(65) Prior Publication Data

US 2024/0315734 A1 Sep. 26, 2024

(51) Int. Cl.
    *A61B 17/70* (2006.01)

(52) U.S. Cl.
    CPC .......... *A61B 17/70* (2013.01); *A61B 17/7002* (2013.01)

(58) Field of Classification Search
    CPC ....... A61B 17/808; A61B 17/70; A61B 17/56; A61B 17/28; A61B 17/29; A61B 17/1606
    See application file for complete search history.

(56) References Cited

U.S. PATENT DOCUMENTS

| 5,891,161 | A | * | 4/1999 | Graser | A61B 17/1775 |
| | | | | | 606/148 |
| 8,663,269 | B2 | * | 3/2014 | Randall | A61B 17/7083 |
| | | | | | 606/207 |
| 11,123,117 | B1 | * | 9/2021 | Sweeney | A61B 17/809 |
| 2011/0087292 | A1 | * | 4/2011 | Sandhu | A61B 17/7055 |
| | | | | | 606/279 |
| 2015/0025573 | A1 | * | 1/2015 | Abitbol | A61B 17/8019 |
| | | | | | 606/281 |
| 2018/0103995 | A1 | * | 4/2018 | Ding | A61B 17/285 |
| 2020/0170691 | A1 | * | 6/2020 | Hodgkins | A61B 17/808 |
| 2022/0000650 | A1 | * | 1/2022 | Kim | A61F 5/01 |
| 2022/0008072 | A1 | * | 1/2022 | Baril | A61B 17/0469 |

* cited by examiner

*Primary Examiner* — Eduardo C Robert
*Assistant Examiner* — Holly Joanna Lane
(74) *Attorney, Agent, or Firm* — Sorell, Lenna & Schmidt, LLP

(57) ABSTRACT

A surgical instrument includes a first arm having a first part connectable with a first interface or a second interface of a spinal implant. A second arm includes a second part connectable with the first interface or the second interface. The first part is connectable with the first interface and the second part is connectable with the second interface to dispose the arms in a fixed orientation with the spinal implant. The first part is connectable with the second interface and the second part is connectable with the first interface to dispose the arms in a movable orientation relative to the spinal implant. Systems, spinal constructs, implants and methods are disclosed.

18 Claims, 9 Drawing Sheets

DETAIL A

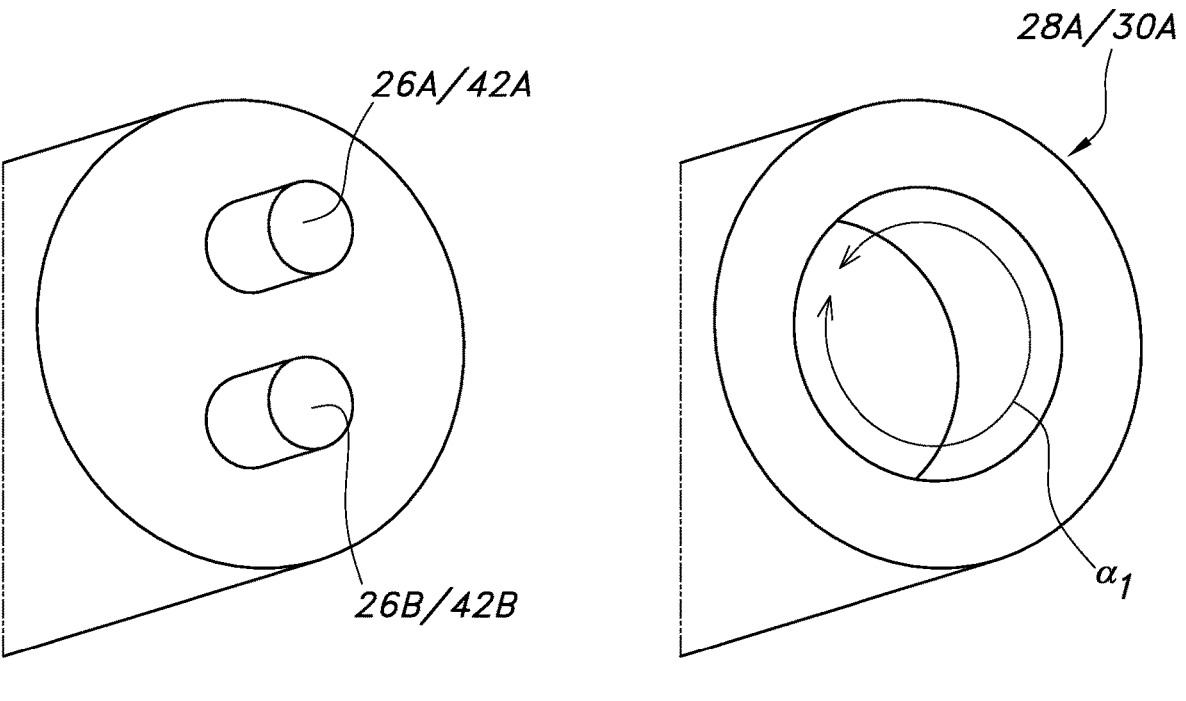
FIG. 4
FIG. 5
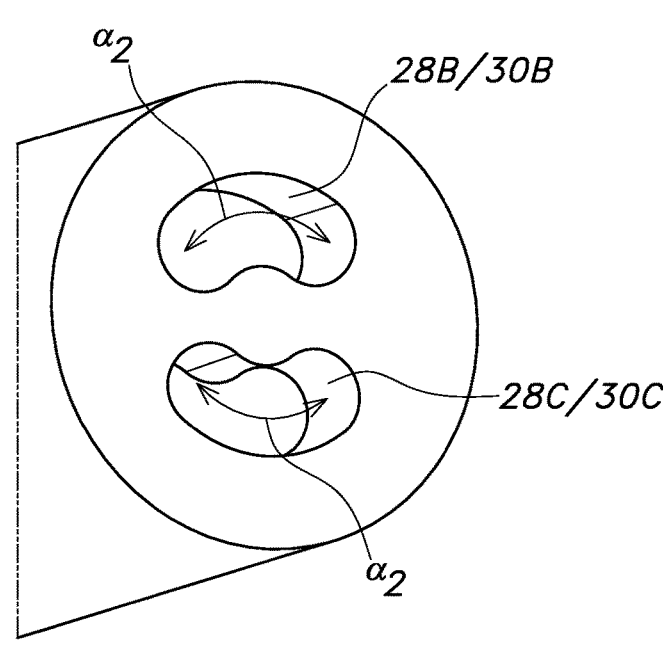
FIG. 6

26C/42C

26D/42D

28D/30D $\alpha_3$ $\alpha_3$

28E/30E

28F/30F $\alpha_4$

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, which can include implants such as connectors, tethers, bone fasteners, plates and vertebral rods are often used to provide stability to a treated region. These implants can redirect stresses away from a damaged or defective region while healing takes place to restore proper alignment and generally support the vertebral members. Surgical instruments are employed, for example, to engage the implants for attachment to one or more vertebral members. This disclosure describes an improvement over these prior technologies.

SUMMARY

In one embodiment, a surgical instrument is provided. The surgical instrument includes a first arm having a first part connectable with a first interface or a second interface of a spinal implant. A second arm includes a second part connectable with the first interface or the second interface. The first part is connectable with the first interface and the second part is connectable with the second interface to dispose the arms in a fixed orientation with the spinal implant. The first part is connectable with the second interface and the second part is connectable with the first interface to dispose the arms in a movable orientation relative to the spinal implant. In some embodiments, systems, spinal constructs, implants and methods are disclosed.

In some embodiments, the surgical instrument includes a first arm having a handle and a jaw having a first projection being engageable with a first recess or a second recess of a spinal implant. A second arm has a handle and a jaw having a second projection being engageable with the first recess or the second recess. The first projection is configured and dimensioned for mating engagement with the first recess and the second projection is configured and dimensioned for mating engagement with the second recess to dispose the arms in a fixed orientation with the spinal implant. The first projection is engageable with the second recess and the second projection is engageable with the first recess to dispose the arms in a movable orientation relative to the spinal implant.

In one embodiment, a spinal implant system is provided. The spinal implant system includes a spinal implant having a first interface and a second interface. A surgical instrument includes a first arm having a first part connectable with the first interface or the second interface. A second arm has a second part connectable with the first interface or the second interface. The first part is connectable with the first interface and the second part is connectable with the second interface to dispose the arms in a fixed orientation with the spinal implant. The first part is connectable with the second interface and the second part is connectable with the first interface to dispose the members in a movable orientation relative to the spinal implant.

BRIEF DESCRIPTION OF THE DRAWINGS

The present disclosure will become more readily apparent from the specific description accompanied by the following drawings, in which:

FIG. 4 is break away perspective view of components of the system shown in FIG. 1;

FIG. 5 is break away perspective view of components of the system shown in FIG. 1;

FIG. 6 is break away perspective view of components of the system shown in FIG. 1;

DETAILED DESCRIPTION

Figure 1:
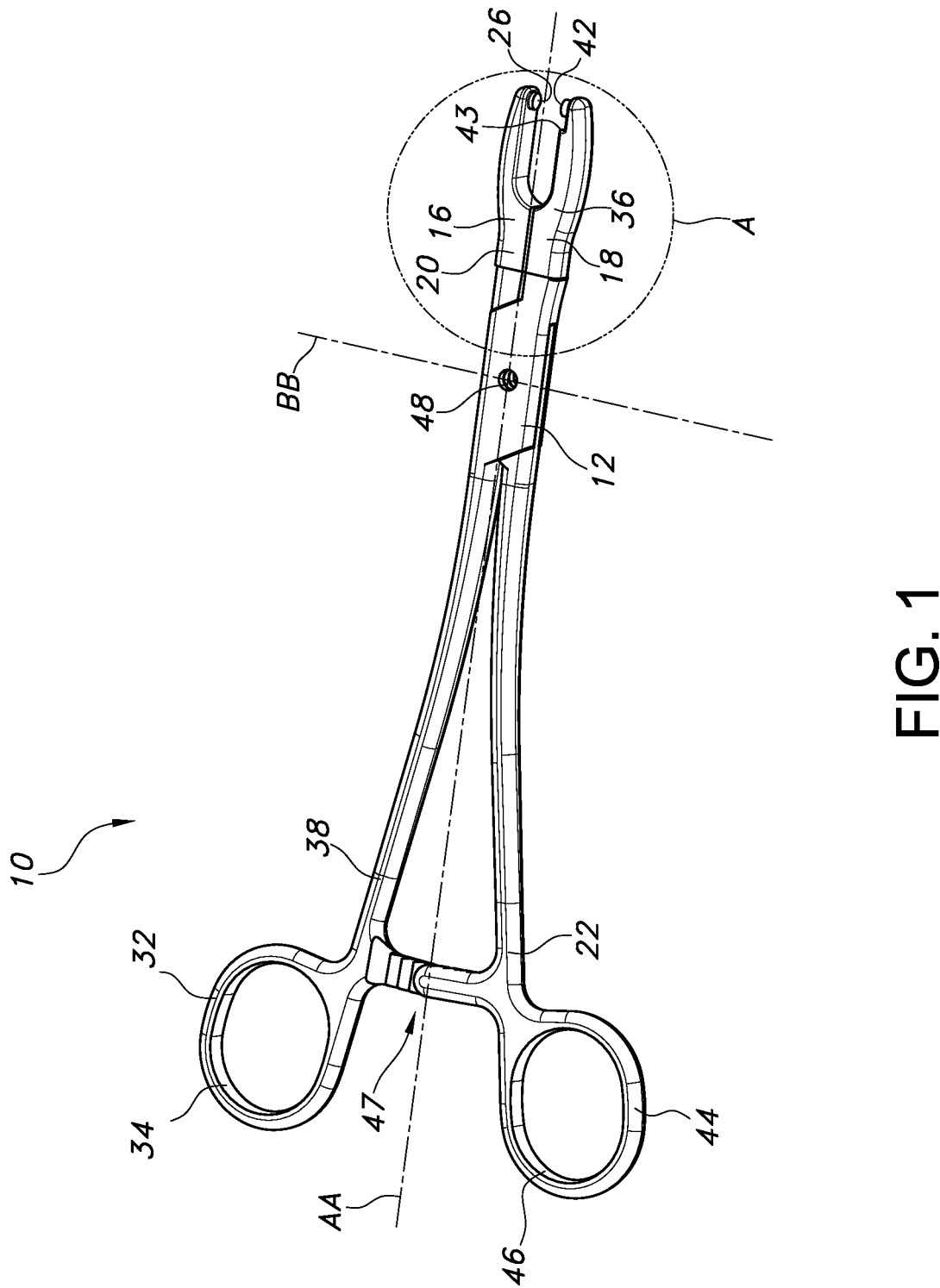
FIG. 1 is a perspective view of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a spinal implant system and method for treatment of a spine disorder. In some embodiments, the systems and methods of the present disclosure are employed with a spinal joint fusion, for example, with a cervical, thoracic, lumbar and/or sacral region of a spine. In some embodiments, the present spinal implant system includes a surgical instrument that can be employed with one or more spinal implants, for example, connectors, tethers, bone fasteners, plates and vertebral rods in a revision and/or reconstruction procedure. In some embodiments, the present spinal implant system may be employed in applications for correction of deformities, such as scoliosis and kyphosis.

In some embodiments, the present spinal implant system includes a surgical instrument, for example, forceps that include a pair of arms that each include a projection. In some embodiments, the projections are configured to matingly engage with recesses of a spinal implant, for example, a connector such that the forceps can engage with the connector in a movable orientation and a fixed orientation. In some embodiments, in the fixed orientation, the forceps are configured to attach to the connector and to fix an angular orientation of the connector for disposal with a spinal implant, for example, a spinal rod. In some embodiments, in the movable orientation, the forceps are configured to attach with the connector such that the connector is freely rotatable relative to the forceps. In some embodiments, connection of the connector to an existing surgery facilitates the addition of new spinal rods that can be attached to existing spinal implants to add length to an existing system. In some embodiments, the forceps add versatility to the system by facilitating either the movable orientation that facilitates an angled control of the connector or the fixed orientation that facilitates a limited angle control when the forceps are attached to the connector. In some embodiments, the forceps facilitate controlled angulation or limited controlled angulation depending on attachment direction.

In some embodiments, the present spinal implant system includes a surgical instrument, for example, forceps, configured for connection with a spinal implant, for example, a connector. In some embodiments, the forceps include a distal end including two opposing faces configured for engagement with two opposing faces of the connector. In some embodiments, the orientation of the faces relates to which orientation the connector is inserted with the forceps. In some embodiments, the orientation of the faces relates to which orientation one inserts the connector with the forceps and defines a desired configuration. In some embodiments, the faces of the forceps and the connector engage in a rigid or a fixed orientation, for example a defined 90 degree angle, and a variable or a movable orientation, for example, a controlled angulation, for example, a defined angle in a range from 70 degrees to 110 degrees, and/or a non-controlled angulation, for example, in a range of 0 to 360 degrees. In some embodiments, the orientations include fixed to fixed at a selected angle, fixed to controlled, controlled to controlled, fixed to non-controlled, and controlled to non-controlled. In some embodiments, the projections include a selected height and a facet to control rotation.

In some embodiments, the present spinal implant system includes a surgical instrument, for example, forceps, configured for connection with a spinal implant, for example, a connector. In some embodiments, the forceps are oriented in an activated or a non-activated configuration. In some embodiments, a distal end of the forceps include one or more projections, for example, a first projection and a second projection configured for engagement with one or more interfaces, for example, a first recess and a second recess configured to control the orientation of the forceps. In some embodiments, the interface includes facets. In some embodiments, the forceps are in a rigid or fixed orientation, and a movable orientation, including, a limited amount of movement and an unlimited amount of movement. In some embodiments, the activated or non-activated configuration is dependent on a height of the projection and/or a depth of the recess.

In some embodiments, the present spinal implant system includes a surgical instrument, for example, forceps that are configured for connection with a spinal implant, for example, a connector. In some embodiments, the forceps are implemented to engage the connector in a revision for an implanted posterior stabilization surgery for patients with proximal junctional kyphosis (PJK) issues. In some embodiments, the forceps include a pair of arms. In some embodiments, each arm includes an end that includes a projection. In some embodiments, the forceps include a short projection and a long projection relative to the short projection. In some embodiments, the projections include pegs. In some embodiments, the short projection is configured for attachment to a shallow hole in the connector and the long projection is configured for attachment to a deep hole in the connector such that the connector is held rigid at a predetermined angle. In some embodiments, the short projection is configured for attachment in the deep hole and the long projection is configured for attachment to the shallow hole such that the connector can be angulated at a predetermined amount.

In some embodiments, the present spinal implant system includes forceps that can be employed in a revision surgery to connect the connector to an existing rod implanted with a body. In some embodiments, the spinal implant system includes one or more revision minimally invasive surgical connectors. In some embodiments, the forceps are configured to attach the connector to one or more existing spinal constructs implanted with a body. In some embodiments, the forceps can be employed in a revision surgery to extend an existing screw and rod construct via the connector. In some embodiments, the forceps can be employed in a revision surgery to connect the connector to an existing spinal construct and extend the existing spinal construct to span one or more spinal levels.

In some embodiments, the present spinal implant system is employed with a method of revision surgery to treat diseases where the discs above and/or below an existing construct begin to deteriorate and may be fused.

In some embodiments, one or all of the components of the spinal implant system may be disposable, peel-pack, prepacked sterile devices. One or all of the components of the system may be reusable. The system may be configured as a kit with multiple sized and configured components.

In some embodiments, the spinal implant system of the present disclosure may be employed to treat spinal disorders for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, for example, in training, testing and demonstration.

The spinal implant system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a spinal implant system including a surgical instrument, for example, forceps engageable with a spinal implant, for example, a connector, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-22, there are illustrated components of a surgical system, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of spinal implant system 10 are configured for engagement with existing spinal constructs, which may include spinal implants such as one or more rods, fasteners, plates and connectors, attached with vertebrae in a revision surgery to manipulate tissue and/or correct a spinal disorder, as described herein. In some embodiments, one or more of the components of spinal implant system 10 can be employed in a revision surgery to connect an existing spinal construct, for example, an existing spinal rod and extend the existing spinal construct to span one or more spinal levels. In some embodiments, the components of spinal implant system 10 is configured for use in PJK revision.

Spinal implant system 10 includes a surgical instrument, for example, forceps 12 configured for engagement with a spinal implant, for example, a connector 14, as shown in FIGS. 1 and 10-12. Forceps 12 are configured for engagement with connector 14 in a rigid or fixed orientation to lock the angulation of forceps 12 relative to connector 14 and/or are configured for engagement with connector 14 in a variable or movable orientation, for example, a controlled angulation and/or or a non-controlled angulation, such that angulation of connector 14 is rotatably adjustable via forceps 12, as described herein. In some embodiments, forceps 12 are configured to facilitate either an angled or limited angle control of connector 14 when forceps 12 are attached to connector 14. In some embodiments, in the movable orientation, forceps 12 are configured to facilitate controlled angulation and/or non-controlled angulation of connector 14, and in the fixed orientation, forceps 12 are configured to facilitate limited controlled angulation of connector 14 depending on connector 14 attachment direction to a spinal implant, for example, a spinal rod 100.

Figure 3:
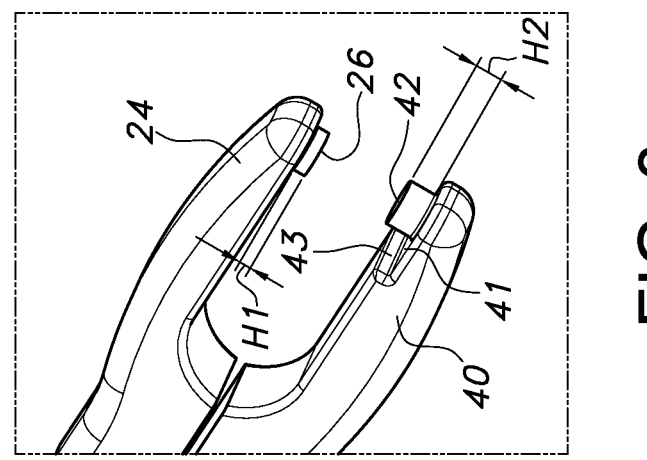
FIG. 3 is break away perspective view of components of the system shown in FIG. 1.
Figure 2:
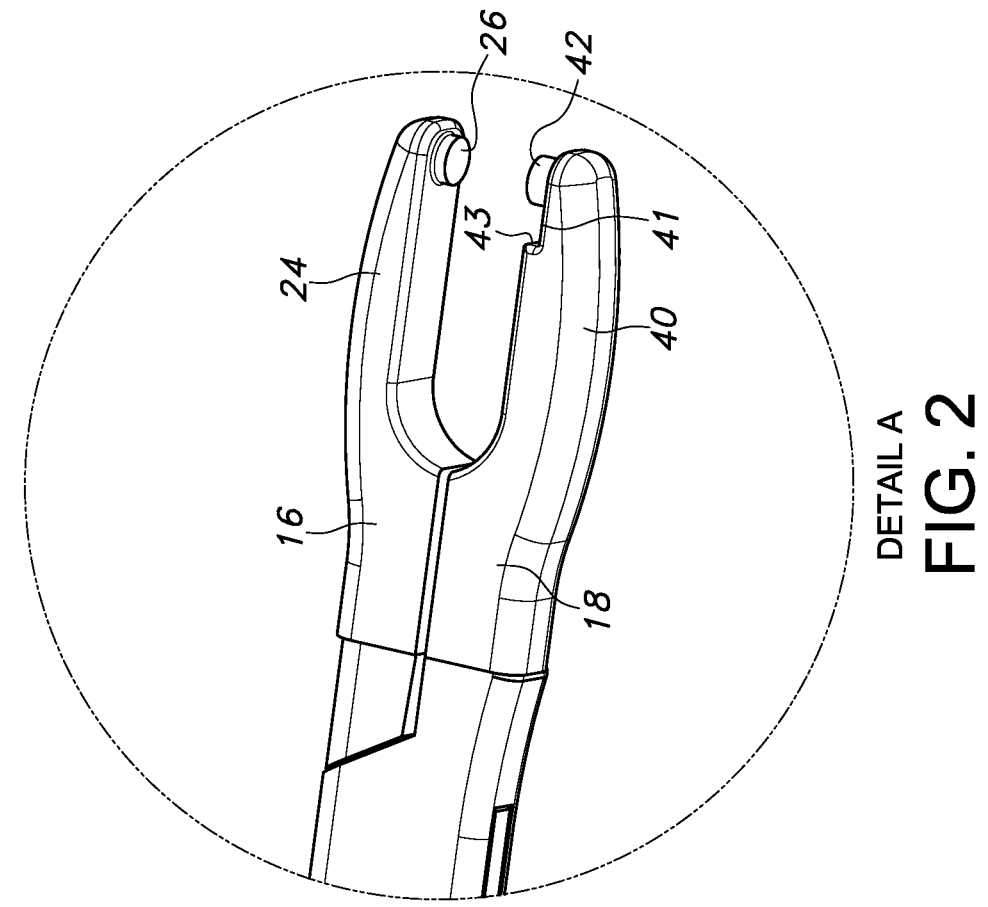
FIG. 2 is an enlarged view of detail A shown in FIG. 1.

Forceps 12 define a longitudinal axis AA, and include an arm 16 and an arm 18, shown in FIGS. 1-3. Arm 16 includes a distal portion 20 and a proximal portion 22. Portion 20 includes a jaw 24 configured for capture of connector 14. Jaw 24 includes a face including a first part, for example, a projection 26, as shown in FIGS. 2-3. Projection 26 is connectable and dimensioned in a mating engagement with an interface or facet, for example, a recess 28 or an interface or facet, for example, a recess 30 of connector 14, as shown in FIGS. 10-13 and 15. In some embodiments, projection 26 is configured and dimensioned for mating engagement with recess 28, as described herein. In some embodiments, projection 26 includes a peg or a pin.

Projection 26 includes a selected height H1, shown in FIG. 3. In some embodiments, height H1 includes a selected height in a range of 1 mm to about 10 mm. In some embodiments, height H1 is 1 mm. In some embodiments, projection 26 may be variously configured including, for example, round, oval, polygonal, irregular, consistent, variable, uniform and non-uniform.

Portion 22 includes a handle 44, as shown in FIG. 1. In some embodiments, handle 44 includes a loop 46 configured for engagement with a user, for example, one or more fingers of a user's hand. Handle 44 is configured to facilitate movement of arm 16. In some embodiments, handle 44 and/or loop 46 include a surface configured to facilitate enhanced gripping of forceps 12. In some embodiments, the gripping surface is textured.

Arm 18 includes a distal portion 36 and a proximal portion 38. Portion 36 includes a jaw 40 configured for capture of connector 14. Jaw 40 includes a face including a first part, for example, a projection 42, as shown in FIGS. 2-3. Projection 42 is connectable and dimensioned in a mating engagement with recess 28 or recess 30 of connector 14, as shown in FIGS. 10-13 and 15. In some embodiments, projection 42 is configured and dimensioned for mating engagement with recess 30, as described herein. In some embodiments, projection 42 includes a peg or a pin.

Projection 42 includes a selected height H2, shown in FIG. 3. Height H2 is greater than Height H1 of projection 26. In some embodiments, height H2 includes a selected height in a range of 1 mm to about 15 mm. In some embodiments, height H2 is 2 mm. In some embodiments, projection 42 may be variously configured including, for example, round, oval, polygonal, irregular, consistent, variable, uniform and non-uniform.

A surface 41 of jaw 40 defines a wall 43, as shown in FIGS. 2-3. Wall 43 is configured to engage with a surface 45 of connector 14 such that when projection 42 engages with recess 30 in the fixed orientation, forceps 12 is fixed with connector 14 and rotation of connector 14 relative to forceps 12 is prevented. In some embodiments, wall 43 includes a textured surface, including a knurled and/or dimpled surface, that is configured to facilitate enhanced fixation with connector 14.

In some embodiments, as shown in FIG. 4, jaw 24 alternatively includes a pair of pegs 26A, 26B, and jaw 40 alternatively includes a pair of pegs 42A, 42B, similar to projections 26, 42. Pegs 26A, 26B and pegs 42A, 42B are connectable and dimensioned in a mating engagement with an interface or facet, for example, a recess 28A, 30A, for a non-controlled angle α1 in the movable orientation, as shown in FIG. 5. In some embodiments, the non-controlled angle is in a range of 0 to 360 degrees. In some embodiments, pegs 26A, 26B and pegs 42A, 42B are connectable and dimensioned in a mating engagement with an interface or facet, for example, recesses 28B, 28C and recesses 30B, 30C, for a controlled angle configuration α2, as shown in FIG. 6. In some embodiments, the controlled angle is in a range from 70 degrees to 110 degrees.

Figure 7:
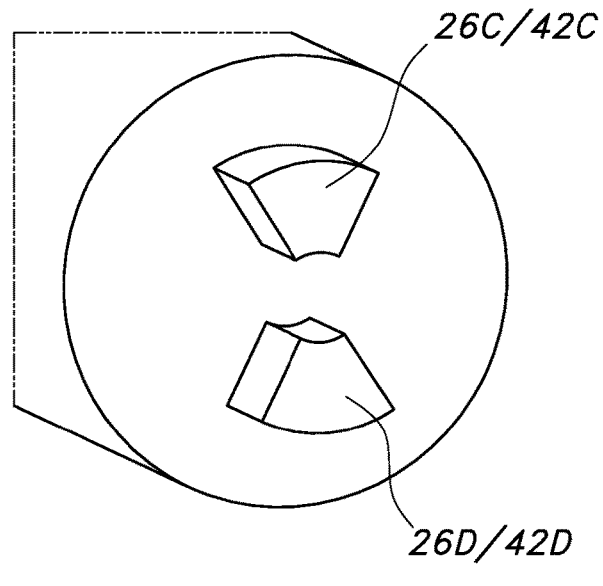
FIG. 7 is break away perspective view of components of the system shown in FIG. 1.
Figure 8:
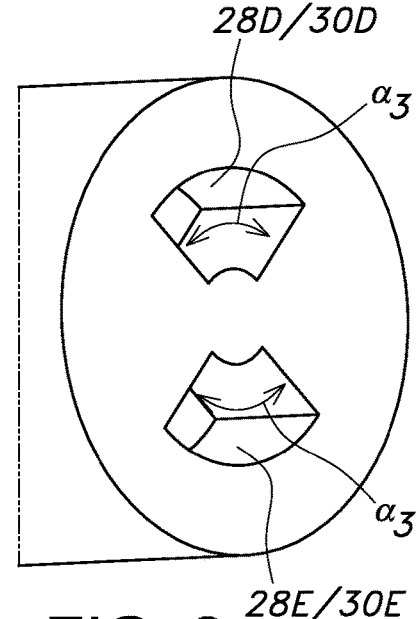
FIG. 8 is break away perspective view of components of the system shown in FIG. 1.
Figure 9:
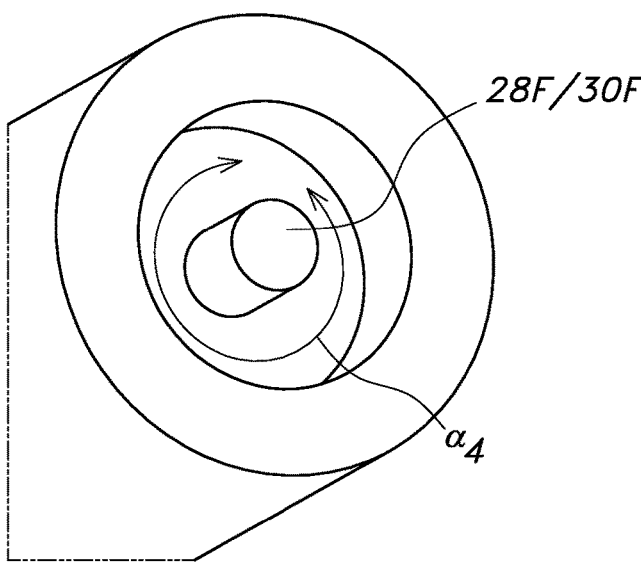
FIG. 9 is break away perspective view of components of the system shown in FIG. 1.

In some embodiments, as shown in FIG. 7, jaw 24 alternatively includes a pair of wedges 26C, 26D, and jaw 40 alternatively includes a pair of wedges 42C, 42D, similar to projections 26, 42. Wedges 26C, 26D and wedges 42C, 42D are connectable and dimensioned in a mating engagement with an interface or facet, for example, a peg 28F, 30F, for a non-controlled angle α4 in the movable orientation, as shown in FIG. 9. In some embodiments, the non-controlled angle is in a range of 0 to 360 degrees. In some embodiments, pegs 26C, 26D and pegs 42C, 42D are connectable and dimensioned in a mating engagement with an interface or facet, for example, recesses 28D, 28E and recesses 30D, 30E, for a controlled angle α3 configuration, as shown in FIG. 8. In some embodiments, the controlled angle is in a range from 70 degrees to 110 degrees.

Portion 38 includes a handle 32, as shown in FIG. 1. In some embodiments, handle 32 includes a loop 34 configured for engagement with a user, for example, one or more fingers of a user's hand. Handle 32 is configured to facilitate movement of arm 18. In some embodiments, handle 32 and/or loop 34 include a surface configured to facilitate enhanced gripping of forceps 12. In some embodiments, the gripping surface is textured.

A locking mechanism 47 is disposed between handles 32, 44, as shown in FIG. 1. Locking mechanism 47 is configured to fix arms 16, 18 in a selected orientation. In some embodiments, locking mechanism is configured to fix arms 16, 18 in a selected orientation relative to connector 14. In some embodiments, locking mechanism 47 includes a ratchet configuration.

Arms 16, 18 are connected at a pivot point PP via a pin 48. Pin 48 defines a transverse axis BB, relative to longitudinal axis AA, as shown in FIG. 1. Projections 26, 42 are movable along and/or relative to transverse axis BB for disposal in an aligned orientation in the fixed orientation or the movable orientation.

Figures 10, 11, 12:
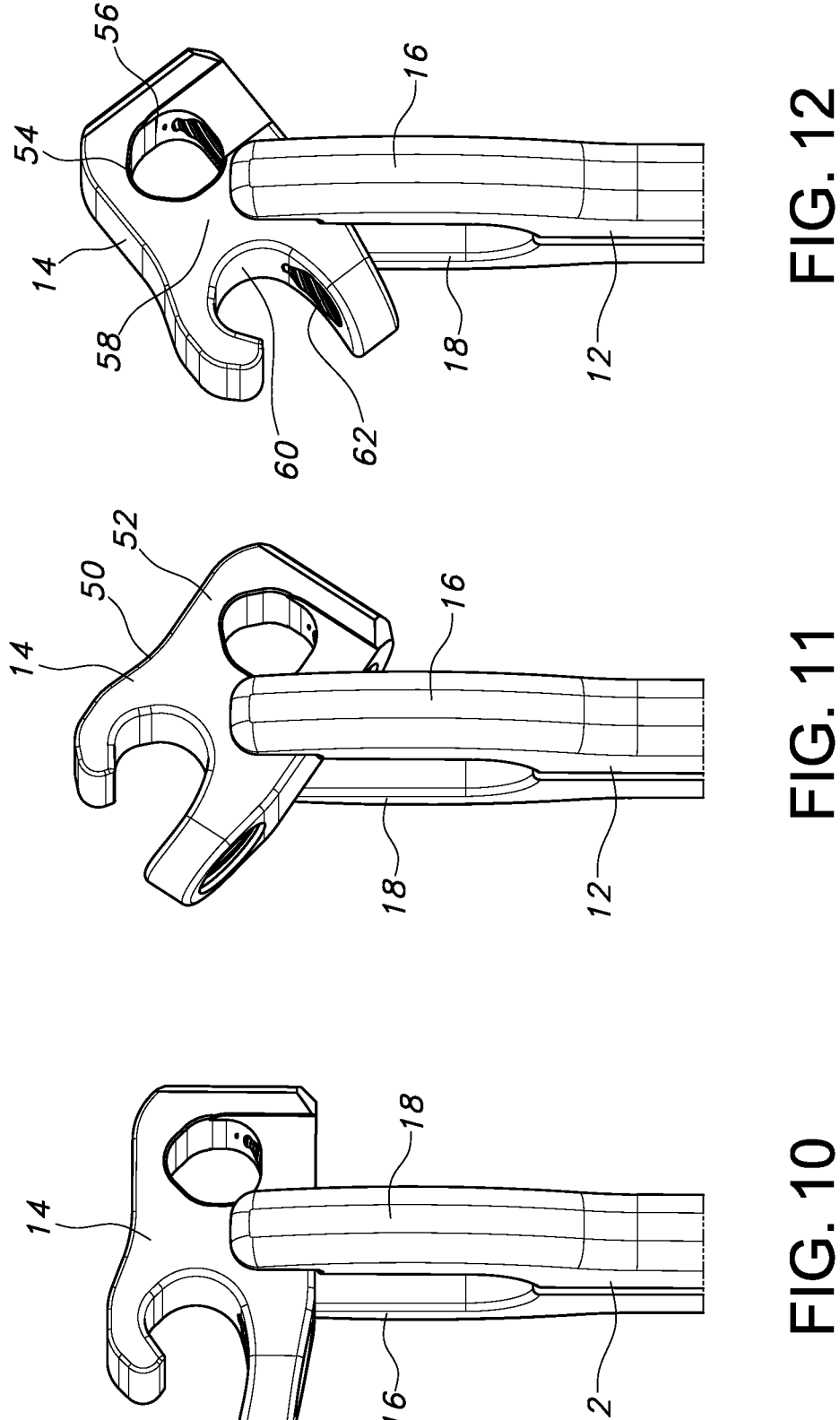
FIG. 10 is a break away perspective view of components of the system shown in FIG. 1.
FIG. 11 is a break away perspective view of components of the system shown in FIG. 1.
FIG. 12 is a break away perspective view of components of the system shown in FIG. 1.
Figure 17:
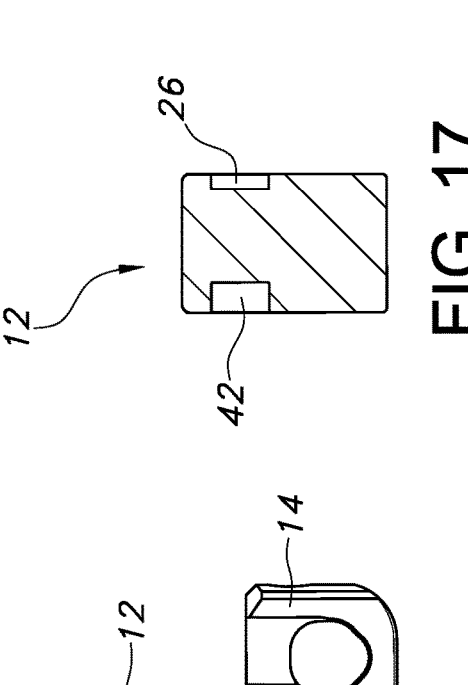
FIG. 17 is a side cross section view of components of the system shown in FIG. 1.
Figure 13:
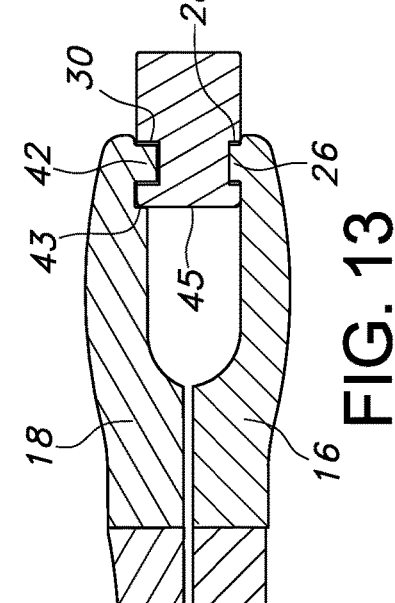
FIG. 13 is a break away cross section view of components of the system shown in FIG. 1.
Figure 15:
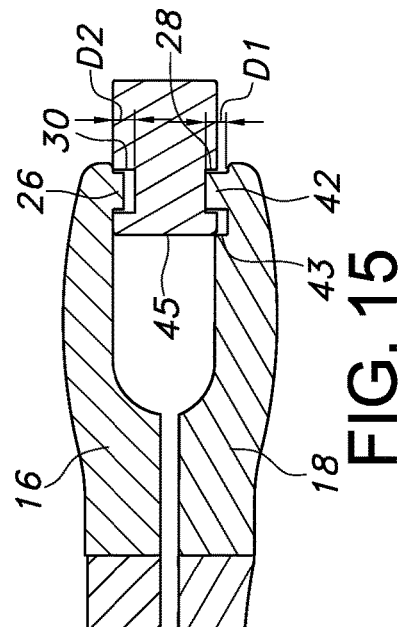
FIG. 15 is a break away cross section view of components of the system shown in FIG. 1.
Figures 18, 19:
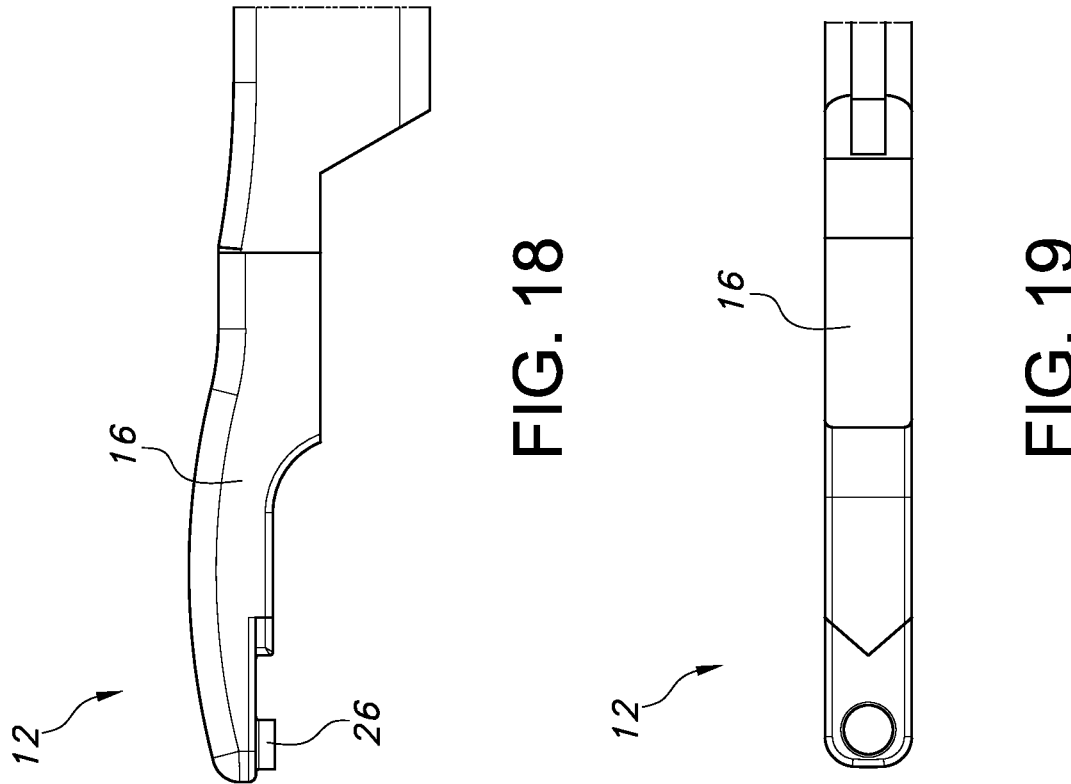
FIG. 18 is a side view of components of the system shown in FIG. 1.
FIG. 19 is a side view of components of the system shown in FIG. 1.
Figures 20, 21:
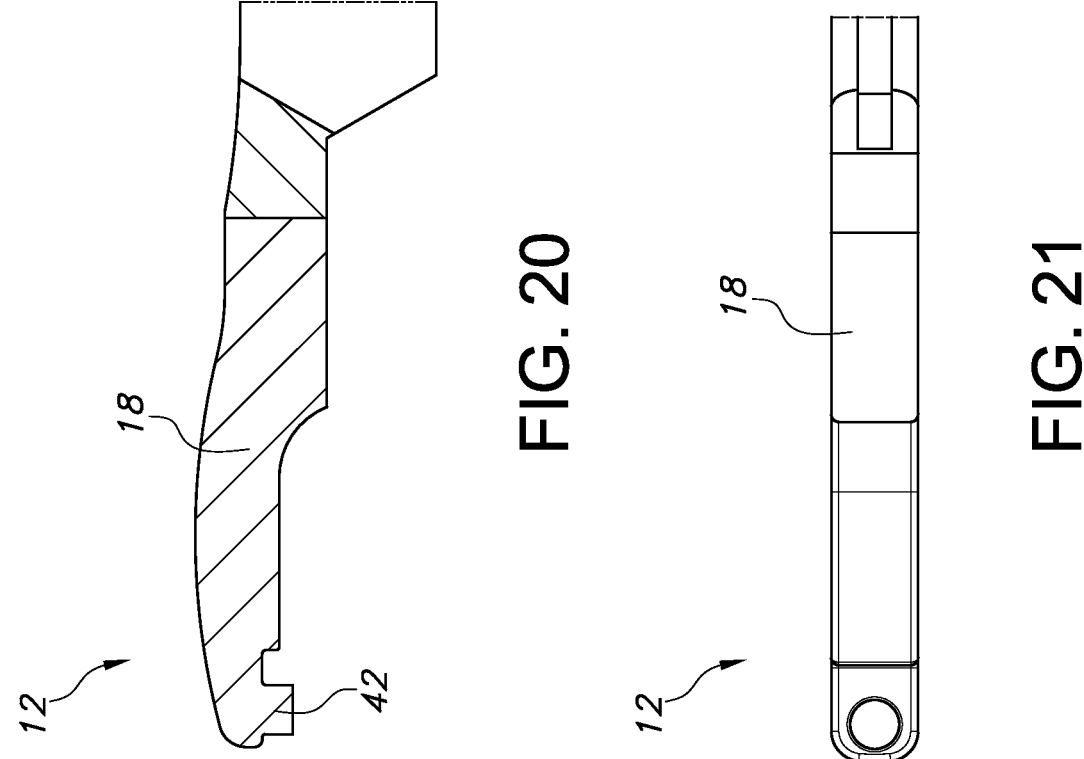
FIG. 20 is a side cross section view of components of the system shown in FIG. 1.
FIG. 21 is a side view of components of the system shown in FIG. 1.

Connector 14 includes a body 50 having a surface 52 that defines recesses 28, 30, as shown in FIGS. 11, 13 and 15. Recess 28 includes a depth D1 and recess 30 includes a depth D2, shown in FIG. 15. Depth D2 is greater than depth D1. In some embodiments, depth D1 and/or depth D2 include a depth of 1 mm to about 15 mm. In some embodiments, recesses 28, 30 may be variously configured including, for example, round, oval, polygonal, irregular, consistent, variable, uniform and non-uniform. In some embodiments, recesses 28, 30 alternatively include a hole, groove or a cavity.

Figure 14:
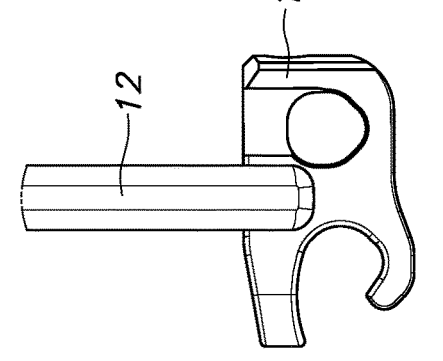
FIG. 14 is a break away side view of components of the system shown in FIG. 1.

Projection 26 is connectable with recess 28 and projection 42 is connectable with recess 30 to dispose arms 16, 18 in the fixed orientation with connector 14. Surface 45 of connector 14 is aligned and disposed in an abutting engagement with wall 43 such that when projection 42 engages with recess 30, forceps 12 is fixed with connector 14 and rotation of connector 14 relative to forceps 12 is prevented. In the fixed orientation, height H1 of projection 26 is similar in dimension to depth D1 of recess 28 to dispose in a flush mating engagement, and height H2 of projection 42 is similar in dimension to depth D2 of recess 30 to dispose in a flush mating engagement, such that connector 14 is held fixed at a predetermined angle relative to forceps 12, as shown in FIGS. 3, 13 and 14. In some embodiments, in the fixed orientation, forceps 12 are connected with connector 14 and are configured to lock angulation of connector 14 relative to forceps 12. In some embodiments, in the fixed orientation, fixed attachment of connector 14 to forceps 12 enables forceps 12 to connect connector 14 to an existing spinal rod or spinal rod 100 while locking the angled orientation of connector 14.

Figure 16:
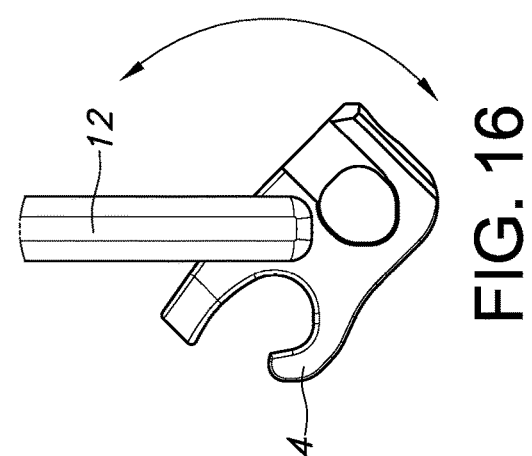
FIG. 16 is a break away perspective view of components of the system shown in FIG. 1.

Projection 26 is connectable with recess 30 and projection 42 is connectable with recess 28 to dispose arms 16, 18 in the movable orientation relative to connector 14, described herein. In the movable orientation, height H1 of projection 26 is shorter than the depth D2 of recess 30, and height H2 of projection 42 is greater than the depth D1 of recess 28 such that projection 42 extends outside of recess 28 to offset wall 43 from surface 45, such that connector 14 can rotate relative to forceps 12, as shown in FIGS. 3, 15 and 16. In some embodiments, in the movable orientation, connector 14 is movable in a perpendicular orientation relative to forceps 12 in an amount of +/−1 to 5 degrees. In some embodiments, in the movable orientation, connector 14 is movable relative to forceps 14 in an amount of 1 to 45 degrees. In some embodiments, in the movable orientation, forceps 12 are configured to adjust angulation of connector 14 to assist connector 14 in connecting to an existing spinal rod or spinal rod 100 where connector 14 is angled in order to connect to the existing spinal rod or spinal rod 100.

Body 50 includes an inner surface 54 that defines a slot 56 configured for disposal of a spinal rod, including spinal rod 100 or an existing spinal rod (not shown) implanted prior to or during the surgical procedure, as shown in FIG. 12. Inner surface 54 defines a wall 58 that defines a bay 60 configured for disposal of spinal rod 100. Inner surface 54 defines a threaded opening 62 configured for engagement with a coupling member, for example, a set screw (not shown) configured to fix spinal rod 100 in a selected orientation with connector 14.

Connector 14 is configured to extend an existing spinal implant without removing the existing spinal implant. In some embodiments, existing spinal implants may include one or more implants connected or fixed with tissue in a prior or different surgical procedure, separate in time and/or over a duration of time in the same surgical procedure.

In some embodiments, bay 60 may be disposed in various orientations, for example, perpendicular, transverse and/or at angular orientations, such as acute or obtuse relative to slot 56. In some embodiments, bay 60 may be disposed offset or staggered from slot 56. In some embodiments, bay 60 and/or slot 56 may have various cross section configurations, for example, oval, oblong, triangular, rectangular, square, polygonal, irregular, uniform, non-uniform, variable and/or tapered. In some embodiments, inner surface 54 may include gripping elements or surfaces that can be, for example, rough, arcuate, undulating, mesh, porous, semiporous, dimpled and/or textured to facilitate engagement with spinal rod 100 and/or an existing spinal rod.

In some embodiments, spinal implant system 10 can include one or a plurality of connectors 14 such as those described herein and/or fixation elements, which may be employed with a single vertebral level or a plurality of vertebral levels. In some embodiments, one or more connectors 14 may be engaged with vertebrae in various orientations, for example, series, parallel, offset, staggered and/or alternate vertebral levels. In some embodiments, one or more connectors 14 may be employed with multi-axial screws, sagittal angulation screws, pedicle screws, monoaxial screws, uni-planar screws, fixed screws, anchors, tissue penetrating screws, conventional screws, expanding screws, wedges, anchors, buttons, clips, snaps, friction fittings, compressive fittings, expanding rivets, staples, nails, adhesives, posts, connectors, fixation plates and/or posts.

In assembly, operation and use, spinal implant system 10, similar to the systems and methods described herein, is employed with a surgical procedure, for example, a surgical treatment of an applicable condition or injury of an affected section of a spinal column and adjacent areas within a body. In some embodiments, spinal implant system 10 includes forceps 12 and connector 14 employed in a surgical treatment such as a revision surgery to extend an existing spinal construct. In some embodiments, spinal implant system 10 includes forceps 12 and connector 14 employed in a revision surgery to connect with an existing spinal construct and extend the existing spinal construct to span one or more spinal levels. In some embodiments, spinal implant system 10 is implemented in a revision for an implanted posterior stabilization surgery for patients with PJK issues. In some embodiments, the existing spinal construct may include one or more implants connected or fixed with tissue in a prior or different surgical procedure, separate in time and/or over a duration of time in the same surgical procedure. In some embodiments, during a surgical treatment, spinal implant system 10 may be completely or partially revised, removed or replaced.

For example, a surgical treatment may include adding length to an existing spinal construct that includes a spinal rod implanted with vertebrae in a prior surgical procedure and spans one or more intervertebral discs. For example, in the prior surgical procedure, the spinal rod is implanted spanning a single vertebral disc to structurally fuse adjacent vertebrae with the existing spinal construct, which includes bone screws connected with the spinal rod to span intervertebral disc. In one example, subsequent or different to the prior surgical procedure, an adjacent disc develops a disorder for treatment. In some embodiments, the treatment of the disc includes connector 14 employed in a revision surgery to connect with the spinal rod to form a revised spinal construct that extends to span spinal levels. In some embodiments, this configuration avoids disruption and tissue damage of the area of the prior surgical procedure, and reduction in healing and treatment duration.

In connection with the revision surgery, to treat a selected section of vertebrae, a medical practitioner obtains access to a surgical site including vertebrae in any appropriate manner, such as through incision and retraction of tissues. In some embodiments, spinal implant system 10 can be used in any surgical method or technique including open surgery, mini-open surgery, minimally invasive surgery and percutaneous surgical implantation, whereby vertebrae is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway to access an existing spinal construct (not shown), including for example, implanted bone screws and one or more implanted spinal rods. The surgical pathway is utilized for implantation of components of spinal implant system 10. A preparation instrument (not shown) can be employed to prepare tissue surfaces of vertebrae, as well as for aspiration and irrigation of a surgical region.

Figure 22:
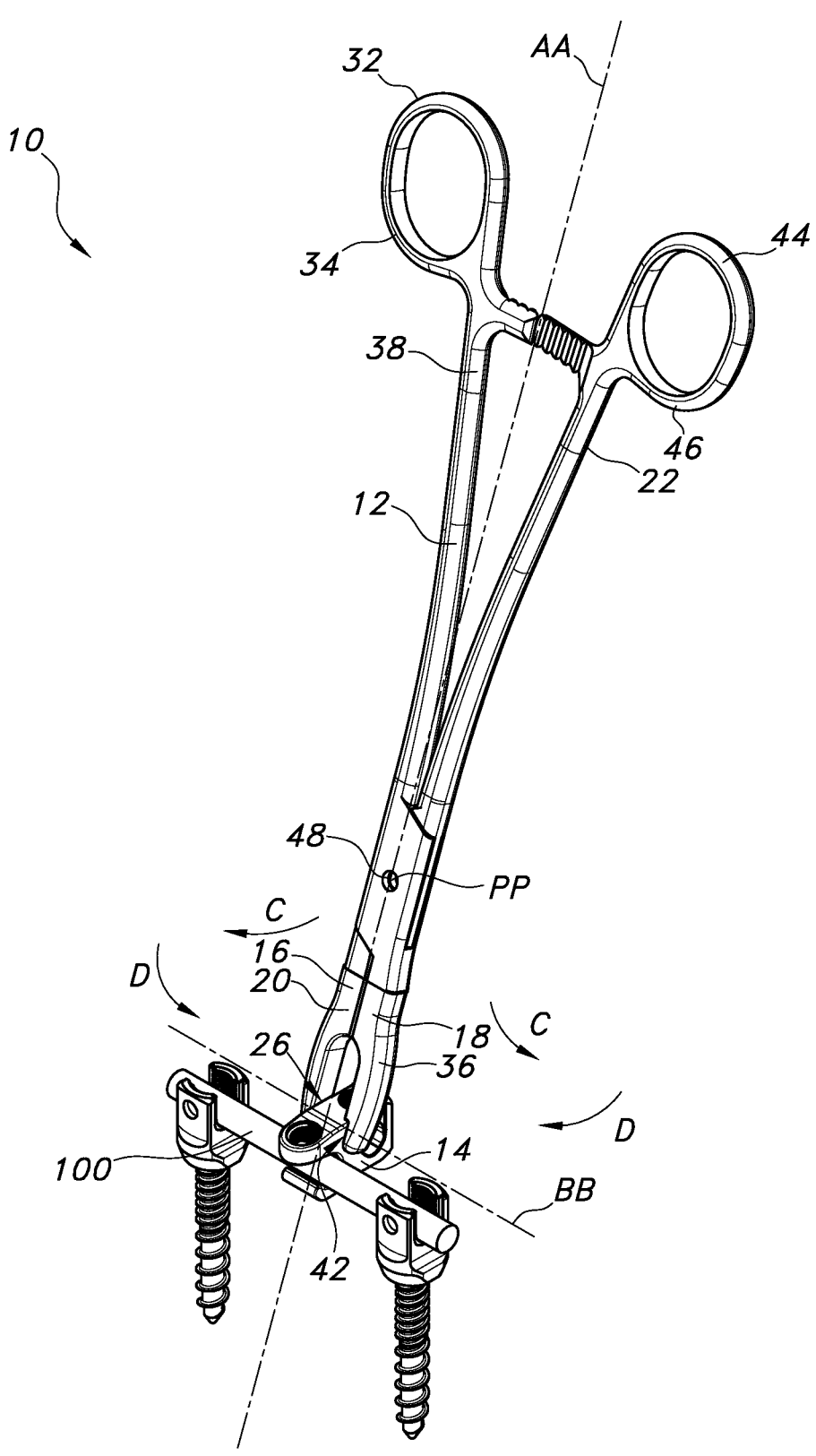
FIG. 22 is a perspective view of components of one embodiment of a system in accordance with the principles of the present disclosure.

Forceps 12 are connected via arms 16, 18 and projections 26, 42 to connector 14 at recesses 28, 30, as shown in FIG. 22. Forceps 12 are configured to engage connector 14 in a fixed orientation to lock the angulation of forceps 12 relative to connector 14 and/or are configured for engagement with connector 14 in a movable orientation such that angulation of connector 14 is rotatably adjustable via forceps 12, as described herein.

Arms 16, 18 are moved in a direction, for example, an outward direction shown by arrows C, relative to pivot point PP and transverse axis BB to expand arms 16, 18 for connection with connector 14. Arms 16, 18 are moved in a direction, for example, an inward direction shown by arrows D, and pivot about pivot point PP to capture connector 14 at recesses 28, 30.

To position forceps 12 in the fixed orientation, projection 26 matingly engages with recess 28 and projection 42 matingly engages with recess 30. Surface 45 of connector 14 is aligned and disposed in an abutting engagement with wall 43 such that when projection 42 engages with recess 30, forceps 12 is fixed with connector 14 and rotation of connector 14 relative to forceps 12 is prevented. In the fixed orientation, height H1 of projection 26 is similar in dimension to depth D1 of recess 28 to dispose in a flush mating engagement, and height H2 of projection 42 is similar in dimension to depth D2 of recess 30 to dispose in a flush mating engagement, such that connector 14 is held fixed at a predetermined angle relative to forceps 12. In the fixed orientation, connector 14 is held fixed and/or rigid at a predetermined angle, as described herein, to attach connector with spinal 100 and/or an existing spinal rod.

To position forceps 12 in the movable orientation, projection 26 matingly engages with recess 30 and projection 42 matingly engages with recess 28 such that connector 14 can be adjusted and angulated at a predetermined amount, to attach connector with spinal 100 and/or an existing spinal rod or to adjust angulation of connector 14. In the movable orientation, height H1 of projection 26 is shorter than the depth D2 of recess 30, and height H2 of projection 42 is greater than the depth D1 of recess 28 such that projection 42 extends outside of recess 28 to offset wall 43 from surface 45, such that connector 14 can rotate relative to forceps 12, as shown in FIGS. 3, 15 and 16. In some embodiments, a selected amount of force is applied to arms 16, 18 to connect forceps 12 with connector 14. In some embodiments, a selected amount of force is applied to securely fix forceps 12 with connector 14. In some embodiments, to maintain a selected amount of angular rotation, a lesser amount of force is applied to forceps 12 when in engagement with connector 14.

Connector 14 is disposed adjacent spinal rod 100 or an existing spinal rod. Connector 14 is manipulated via forceps 12 to dispose and capture spinal rod 100 and/or an existing spinal rod with slot 56 and/or bay 60, as described herein. Connector 14 and rod 100 are configured to extend the existing spinal construct to form a revised spinal construct. In some embodiments, spinal rod 100 is configured to share the load applied to the existing spinal rod.

Connector 14 is configured to extend existing spinal constructs without disruption of the existing spinal constructs. In some embodiments, rod 100 is configured to add support and strength to spinal implant system 10 along selected vertebrae.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a first arm including a first part connectable with a first interface or a second interface of a spinal implant; and
a second arm including a second part connectable with the first interface or the second interface;
the first part being connectable with the first interface to dispose the first arm in a fixed orientation with the spinal implant;
the second part being connectable with the second interface to dispose the second arm in a fixed orientation with the spinal implant;
the first part being connectable with the second interface to dispose the first arm in a movable orientation relative to the spinal implant;
the second part being connectable with the first interface to dispose the second arm in a movable orientation relative to the spinal implant;
the first part including a first projection having a first height;
the second part including a second projection that is coaxial with the first projection, the second projection having a second height greater than the first height;

the first arm and second arm being connected to define a longitudinal axis; and the first part and second part being disposed in alignment along a transverse axis in the fixed orientation and the movable orientation.

2. A surgical instrument as recited in claim 1, wherein the first part is configured and dimensioned for mating engagement with the first interface.

3. A surgical instrument as recited in claim 1, wherein the second part is configured and dimensioned for mating engagement with the second interface.

4. A surgical instrument as recited in claim 1, wherein the first interface includes a first recess having a first depth and the second interface includes a second recess having a second depth greater than the first depth.

5. A surgical instrument as recited in claim 4, wherein the first recess and the second recess are coaxial.

6. A surgical instrument as recited in claim 1, wherein the first projection is configured and dimensioned for mating engagement with the first interface and the second projection is configured and dimensioned for mating engagement with the second interface such that the first arm and second arm are disposed in the fixed orientation with the spinal implant.

7. A surgical instrument as recited in claim 1, wherein the movable orientation includes a controlled angulation and/or a non-controlled angulation.

8. A surgical instrument as recited in claim 1, wherein:

the first arm includes a first jaw having a first planar surface, the first projection extending from the first planar surface; and the second arm includes a second jaw having a second planar surface and a third planar surface that is offset from the second planar surface, the second projection extending from the third planar surface.

9. A surgical instrument as recited in claim 8, wherein the second projection is spaced apart from the second planar surface by a gap.

10. A surgical instrument as recited in claim 1, wherein the spinal implant includes a connector including an inner surface that defines a slot and a wall that defines a bay configured for disposal of a spinal rod.

11. A surgical instrument as recited in claim 10, wherein the bay extends parallel to the slot such that the spinal rod extends parallel to the slot when the spinal rod is disposed in the bay.

12. A surgical instrument comprising:

a first arm including a handle and a jaw having a first projection being engageable with a first recess or a second recess of a spinal implant; and a second arm including a handle and a jaw having a second projection being engageable with the first recess or the second recess, the first projection being configured and dimensioned for mating engagement with the first recess and the second projection being configured and dimensioned for mating engagement with the second recess to dispose the first arm and the second arm in a fixed orientation with the spinal implant, the first projection being engageable with the second recess and the second projection being engageable with the first recess to dispose the first arm and the second arm in a movable orientation relative to the spinal implant, the first projection having a first height;

the second projection having a second height greater than the first height;

the first arm and the second arm being connected to define a longitudinal axis; and the first part and the second part being disposed in alignment along a transverse axis in the fixed orientation and the movable orientation.

13. A surgical instrument as recited in claim 12, wherein the first recess has a first depth and the second recess has a second depth greater than the first depth.

14. A surgical instrument as recited in claim 12, wherein the first arm and the second arm are connected to define a longitudinal axis and the projections are disposed in alignment along a transverse axis in the fixed orientation and the movable orientation.

15. A surgical instrument as recited in claim 12, wherein the spinal implant includes a connector including an inner surface that defines a slot and a wall that defines a bay configured for disposal of a spinal rod.

16. A spinal implant system comprising:

a spinal implant including a first interface and a second interface; and a surgical instrument including a first arm having a first part connectable with the first interface or the second interface, and a second arm having a second part connectable with the first interface or the second interface, the first part being connectable with the first interface and the second part being connectable with the second interface to dispose the first arm and the second arm in a fixed orientation with the spinal implant, the first part being connectable with the second interface and the second part being connectable with the first interface to dispose the first arm and the second arm in a movable orientation relative to the spinal implant, the first part including a first projection having a first height;

the second part including a second projection having a second height greater than the first height;

the first arm and the second arm being connected to define a longitudinal axis; and the first part and the second part being disposed in alignment along a transverse axis in the fixed orientation and the movable orientation, wherein the spinal implant includes a connector including an inner surface that defines a slot and a wall that defines a bay configured for disposal of a spinal rod.

17. A spinal implant system as recited in claim 16, wherein the first arm has a proximal handle portion and a distal portion including the first part and the second arm has a proximal handle portion and a distal portion.

18. A spinal implant system as recited in claim 16, wherein the first projection is configured and dimensioned for mating engagement with the first interface and the second projection is configured and dimensioned for mating engagement with the second interface such that the first arm and the second arm are disposed in the fixed orientation with the spinal implant.

\* \* \* \* \*